Figure 1:
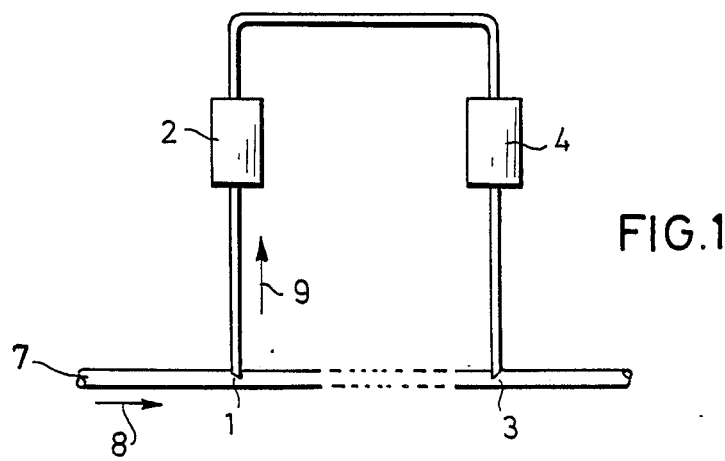

United States Patent [19]

Schmoll et al.

[11] Patent Number: 4,820,261
[45] Date of Patent: Apr. 11, 1989

[54] DEVICE FOR THE REMOVAL OF THERAPEUTIC SUBSTANCES LOCALLY APPLIED FOR USE AGAINST SOLID TUMORS

[75] Inventors: Hans-Joachim Schmoll; Ekkehard Schmoll, both of Hanover; Edmund R. Lax, Essen, all of Fed. Rep. of Germany

[73] Assignee: Bissendorf Peptide GmbH, Fed. Rep. of Germany

[21] Appl. No.: 86,816

[22] Filed: Aug. 19, 1987

[30] Foreign Application Priority Data

Feb. 21, 1987 [DE] Fed. Rep. of Germany ....... 3705637

[51] Int. Cl.$^4$ .............................................. A61M 1/00
[52] U.S. Cl. .......................................... 604/4; 604/5; 604/96
[58] Field of Search ......................... 604/4–6, 604/43, 45, 96, 101, 102

[56] References Cited

U.S. PATENT DOCUMENTS 4,573,966 3/1986 Weikl et al. ........................ 604/101
4,605,394 8/1986 Skurkovich ............................ 604/4
4,614,513 9/1986 Bensinger ................................ 604/6

FOREIGN PATENT DOCUMENTS 3214397 11/1983 Fed. Rep. of Germany .
3523616 1/1987 Fed. Rep. of Germany .

OTHER PUBLICATIONS

Treatment for Unresectable Hepatoma via Selective Hepatic Arterial Infusion of Lymphokine-Activated Killer Cells Generated from Autologous Spleen Cells, Cancer, Sep. 1, 1986, vol. 58, Kiyotaka Okuno, M.D. et al.
Biotechnology in Japan Newsservice, vol. 5, No. 3, Dec. 1986.

Primary Examiner—Stephen C. Pellegrino
Attorney, Agent, or Firm—Wegner & Bretschneider

[57] ABSTRACT

A device for the removal of active substances locally applied against solid tumors consists of a catheter (1) to be positioned distally to the tumor for the collection of blood coming from the tumor, a pump (2) and a catheter (3) connected thereto and returning the blood into the body. The device is characterized in that between the two catheters (1, 3) there is present at least one container (4) capable of allowing blood to pass therethrough and containing immobilized antibodies against the applied active substance.

5 Claims, 3 Drawing Sheets

DEVICE FOR THE REMOVAL OF THERAPEUTIC SUBSTANCES LOCALLY APPLIED FOR USE AGAINST SOLID TUMORS

The present invention relates to a device for the removal of therapeutically active substances locally applied against solid tumors, which device consists of a catheter to be positioned distally to the tumor for the collection of blood coming from the tumor, a pump and a catheter connected thereto and returning the blood into the body.

In vitro investigations with cell cultures of human and animal cells and in vivo studies with species-specific tumors transplanted into animals and human tumors have shown that many Biological Response Modifiers (BRMs) may exert an antineoplastic effect. The term "Biological Response Modifiers" comprises a group of proteins and glycoproteins which are released from a cell and exert an influence on other cells or on the BRM-preparing cell itself, said influence becoming manifest by changes in metabolism or other functions of the cell. In a strict sense, the term is intended to designate the secreted active substances of blood cells and blood cell precursors—e.g. interferons, interleukins, colony stimulating factors, tumour necrosis factor, lymphotoxins, transforming growth factors and/or further stimulating or inhibiting factors—and all other factors which today are connected with the terms lymphokine, monokine and cytokine. As far as known, the antineoplastic activity in vivo, on the one hand, is due to a systemic stimulation of the own immune defense, while, on the other hand, in vitro experiments and xenograft studies suggest that a direct cytotoxic destruction of the tumor cells themselves or their associated blood vessels occurs. Thus, a local reaction takes place. In many of the BRMs the difference between the effective dose and the toxic dose (therapeutic breadth) for man is either very small or does not even exist at all, if the toxic effects prevail. Thus, for example, patients treated with Interleukin-2 (IL-2) must be cared for in an intensive care unit.

Okuno et al., Cancer 58 (1986), pp. 1001–1006, describe a method wherein patients suffering from liver carcinoma (hepatoma) had been treated by means of an arterial infusion with autologous spleen cells which had been previously activated in vitro with IL-2. In a similar way another Japanese group attempted to treat liver cancer with lymphocytes injected into arteries leading to the liver, wherein the injected lymphocytes were to be activated by simultaneous continous infusion of small amounts of IL-2 (see Biotechnology in Japan, News Service, Vol. 5, No. 3, December 1986).

The new method of regional application of toxic active substances offers a possibility to medicine to mitigate these problems by use of a regionally applied dose which is much in excess of the threshold value of systemic toxicity.

The method for the treatment of solid tumors with BRMs according to the present invention is characterized in that BRMs are administered at a high dose in an afferent vessel in the vicinity of the tumor and in an efferent vessel are passed to the blood circulation system and diluted there. Thereby, the dose of the active substance to be employed can be enormously increased. The method is suitable for the treatment of solid tumors, more specifically of tumors of the large pelvis, the liver and the extremities. The improved dosing by means of the method according to the invention can be exemplified by a liver tumor. The liver amounts to about 3% of the total body mass. Thus, using regional perfusion about 35 times the dose of the involved active substance can be employed.

The method also allows a combined and/or sequential application of the BRM with 1. chemotherapeutics;
2. a second BRM;
3. a monoclonal antibody;
4. cytotoxics bonded to monoclonal antibodies;
5. factors sensitizing the tumor or tumor tissue.

A sensitization of the tumor cells, for example, is effected by gamma-interferon which is supposed to increase the number of receptors for the BRMs (Aggarwal et al., Nature 318, 665–667, 1985, "Characterization of receptors for human tumour necrosis factor and their regulation by gamma-interferon"; Balkwill et al., Cancer Res. 46, 3990–3993, 1986, "Human tumour xenografts treated with recombinant human tumor necrosis factor alone or in combination with interferons"; Fransen et al., Eur. J. Cancer Clin. Oncol. 22, 419–426, 1986, "Recombinant tumor necrosis factor: its effect and its synergism with interferon-gamma on a variety of normal and transformed human cell lines"). Actinomycin D is also capable of sensitizing tumor cells (Bersani et al., Immunology 59, 323–325, 1986, "Involvement of tumour necrosis factor in monocyte-mediated rapid killing of actinomycin D-pretreated WEHI 164 sarcoma cells"; Creasy et al., Biological Therapy of Cancer: A 1986 Update, Chapel Hill 1986, "Studies on the cytotoxicity of tumor necrosis factor in vitro").

A large portion of the BRM is adsorbed by the tumor or tumor-containing organ. However, the remainder must be sufficiently diluted in the systemic circulation so tat toxic phenomena do not occur. But, if it is desired to administer the active substance at a dosage which causes toxic phenomena to occur even using the dilution measures described above, the toxic effects can be avoided only by removing the excess of the active substance. For the removal of the BRM it is not advisable to employ the conventional methods of blood filtration, since the BRM's are relative large polar molecules. For example, in the case of toxic reactions blood is passed over an activated carbon filter. Said filters have the drawback that they are non-specific. In addition, they cannot be used for the filtration of biopolymers, more specifically of peptides and proteins from blood for the reason that the range of application of the activated carbon filters is limited to relatively small non-polar compounds. On the other hand, the membranes conventionally used in the dialysis/hemofiltration have only small pore sizes so that the BRMs will nòt permeate into the dialyzate and, thus, cannot be removed.

If the pores of the dialysis membrane are enlarged, then, in addition to the active substances (BRMs) proteins also enter the dialyzate, the removal of which is not desired. The non-specifity of a membrane having sufficiently large pores for separating administered BRM would result in unnecessarily endangering the patient by stressing the patient's metabolism.

Thus, it is the object of the present invention to provide a device which enables the removal from the blood of substances active against tumors so that the active substances can be employed at an otherwise toxic dosage. Such a device is intended also to enable the specific removal of the active substance. A further demand is that the device allows a combined and/or sequential application of
1. chemotherapeutics and BRM;
2. two different BRMs;
3. BRM and monoclonal antibodies;
4. BRM and cytotoxics bonded to monoclonal antibodies; and
5. factors sensitizing the tumor or tumor tissue together with BRM.

The object of the present invention is attained by providing a device for the removal of active substances locally applied to solid tumors, which device consists of a first catheter (1) to be positioned distally to the tumor for the collection of blood coming from the tumor, a pump (2) and a second catheter (3) connected thereto and returning the blood into the body. The device is characterized in that between the two catheters (1, 3) there is present at least one container (4) capable of allowing blood to pass therethrough which contains immobilized antibodies against the applied active substance.

A preferred embodiment of the device according to the invention is the embodiment comprising the two catheters (1) and (3) as a double catheter wherein the first catheter (1) is shorter than the second catheter (3). Double catheters are well known as so-called Aigner catheters in clinical practice. In another embodiment of the device according to the invention, an inflatable balloon (6) is present distally to the opening of the catheter (1) for blood collection which serves as a shut-off means for the blood vessel. This embodiment has the advantage over the open arrangement that excess active substance cannot escape in the direction of the venous blood flow due to diffusion or venous blood flow and all of the blood being accumulated distally to the tumor has to pass through the container (4). It is also possible to locate a second inflatable balloon (6) upstream before the blood vessels exiting from the tumor in order to completely close-off the blood vessel. In this embodiment the collection opening of the catheter (1) is between the two balloons (6).

In the container (4) of the device of the invention there are immobilized antibodies against active substances from blood cells and/or blood cell precursors. Also usable in the device according to the invention are antibodies against substances of the class comprising lymphokines, monokines and/or cytokines, more specifically interferons, interleukins, colony stimulating factors, tumour necrosis factor, lymphotoxin, transforming growth factors and/or further stimulating or inhibiting factors. The device according to the invention meets the requirement set therefor, namely, suitability not only for the administration of single preparations, but also for combination therapies, more particularly
1. a combination of chemotherapeutics and BRM; such therapies are clinically more efficient than the sole administration of single preparations. The BRM is neutralized by monoclonal antibodies and removed. The chemotherapeutic may be removed—if desired—by means of activated carbon, hemofiltration or monoclonal antibodies.
2. a combination of two different BRMs; both of the BRMs are neutralized and removed by monoclonal antibodies.
3. a combination of BRM and monoclonal antibodies (MABs).
4. a combination of BRM and MAB-bound cytotoxic compounds (targeted chemotherapy). BRM as well MAB-derivatives can be removed by the appropriate MABs.
5. a sensitization of the tumor tissue; due to the presence of the permanent arterial catheters it is possible to perfuse the tumor several times and with different agents. This fact is utilized for increasing the sensitivity of the tumor tissue by means of pre-treatment. This pre-treatment consists of a perfusion with compounds which sensitize the cells to the BRMs or the combination therapeutics. The sensitization may be effected by an increase in the number of the BRM receptors, the de novo induction of receptors previously not present, alterations in the intracellular BRM metabolism or other cellular events.

The active substance which may be administered by means of the device the invention is understood to include substances capable of sensitizing the tumor or tumor tissue.

FIG. 1 shows a highly schematic graphic representation of the device according to the invention. In a vein (7) exiting from a tumor or tumor tissue, at a location distal to the tumor there has been inserted the opening of the venous catheter (1). The blood flow direction is indicated by the arrow (8). By means of the pump (2) the blood is drawn in the direction of the arrow (9) through the opening of the venous catheter (1), forced through the container (4) containing immobilized antibodies against the applied active substance and returned to the blood circulation system at the inlet of the venous catheter (3) inserted in the same or a different blood vessel. In the course thereof the antibodies present in the container (4) bind the excess of the applied active substance and remove it from the blood circulation.

Figure 2:
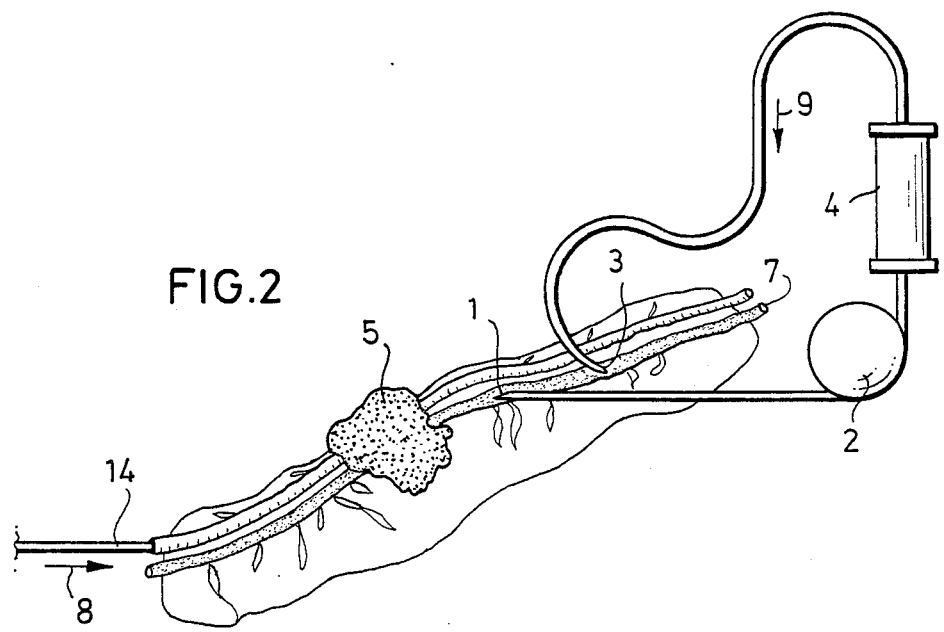

FIG. 2 schematically shows an embodiment of the device according to the present invention, by means of which embodiment a local application against solid tumors of the active substance can be carried out through an arterial catheter (14). In a vein (7) exiting from an intestinal tumor (5) at the side distal to the tumor (5) there has been inserted the opening of the venous catheter (1). The direction of the blood flow is indicated by arrow (8). By means of the pump (2) the blood is aspired in the direction of the arrow (9) through the opening of the venous catheter (1), forced through the container (4) containing immobilized antibodies against the applied active substance and returned to the blood circulation system at the inlet of the venous catheter (3), inserted in the vein (7) at a different location. In the course thereof the antibodies present in the container (4) will bind the excess of the applied active substance and remove same from the blood circulation. Through the arterial catheter there may also be applied the substances sensitizing the tumor.

Figure 3:
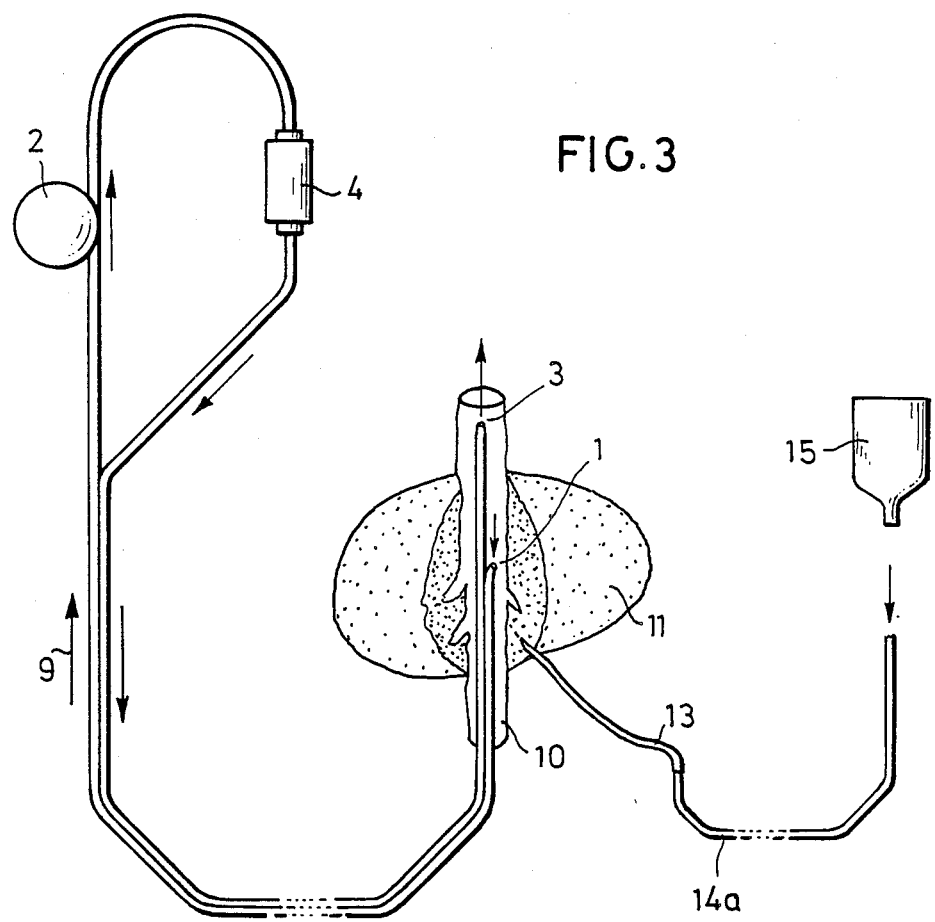

FIG. 3 shows schematically the embodiment in the form of a double catheter to which double catheter has been inserted in the Vena cava (10) for the treatment of a liver tumor (11). By means of an arterial catheter (14a) the active substance (for example BRM) from the supply vessel (15) is locally applied through the Arteria hepatica (13) in the vicinity of the tumor or tumor tissue. The excess active substance discharged into the blood stream from the tumor (for example BRM) is removed together with the blood through the opening of the venous catheter (1) by means of the pump (2), forced through the container (4) containing the immobilized antibodies against the applied active substance and returned to the blood circulation system via the opening of the venous catheter (3).

Figure 4:
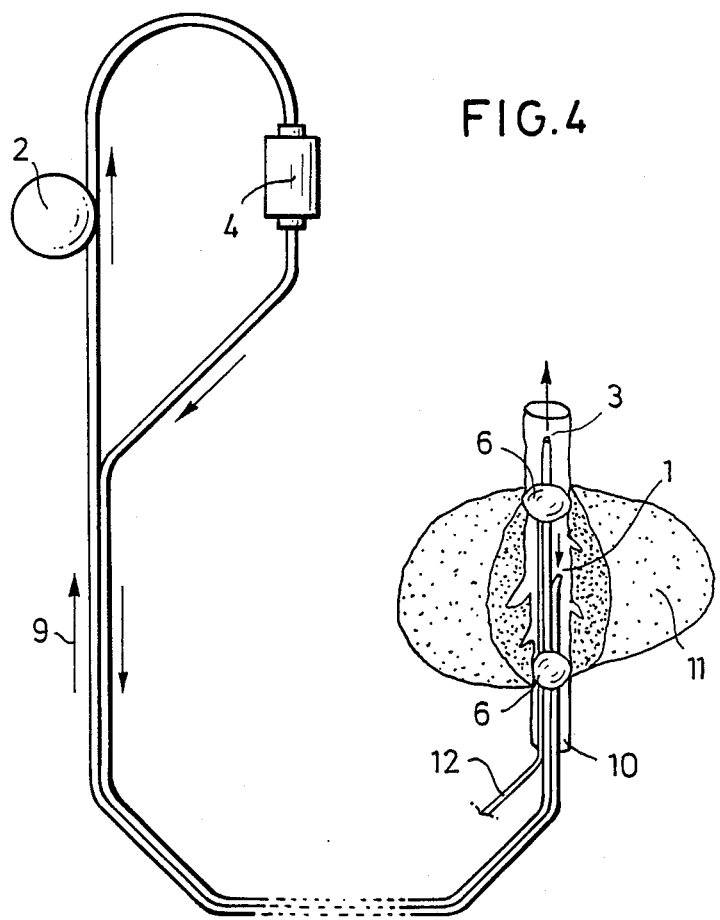

FIG. 4 schematically shows the embodiment in the form of a double catheter, which double catheter has been inserted in the Vena cava (10) for the treatment of a liver tumor (11). Between the balloons (6), inflatable through the air line (12), there is positioned the opening of catheter (1) for collecting the blood, which is returned into the blood stream through the opening (3) of the double catheter on the other side of the balloon (6) in the upstream position, after the collected blood has been forced by means of the pump (2) through the container (4) containing the antibody.

The device of the invention is suitable for use in a perfusion method for the treatment of solid tumors by local application of substances which are active against the tumors, in which method the blood is collected at a location distal to the tumor by means of a catheter, is pumped through a container containing carrier-bound antibody against the active substance and returned into the body. A particular embodiment of the method utilizes the shut-off effect provided by an inflatable balloon (6) positioned distally to the opening of the catheter (1) for collecting the blood. This embodiment is particularly advantageous since it prevents the toxic active substance from being uncontrollably distributed in the body due to diffusion or venous blood flow. The shut-off barrier also ensures that all of the blood being accumulated distally to the tumor passes through the container (4).

The device of the invention also allows a perfusion method to be carried out in the course of which the tumor or tumor tissue is sensitized by the application of active substances.

As the active substances sensitizing the tumor or tumor tissue, there are particularly considered lymphokines. It is further made possible to apply a method wherein BRM as an active substance is combined with 1. chemotherapeutics;
2. a second BRM;
3. a monoclonal antibody; and
4. a cytotoxic compound bonded to a monoclonal antibody.

A procedure adopted for permanent perfusion is also provided by using the device of the invention. This method can be used with all organs, tumors and parts of the body suitable for application of perfusion, for example pelvis tumors, liver tumors, tumors of the extremities etc.

The use of immobilized antibodies against active substances for the treatment of tumors serves to remove the excess of active substance which otherwise would cause toxic phenomena to occur in the patient.

The antibodies active against the active substances to be applied may be immobilized on any suitable carrier. One carrier suitable for the antibodies to be bound, for example, is activated agarose, and particularly Sepharose ®. This matrix, for example, is encapsulated in cellulose bodies having a suitable pore size, filled into the container (4) and sterilized (e.g. by means of gamma rays). Under sterile conditions the antibody is then introduced into the container (4) so that a conjugation between the antibody and the matrix takes place. The excess of antibody may be removed from the container with a sterile saline solution.

The invention is further illustrated by way of the following Example.

EXAMPLE 1

Tumor Necrosis Factor (TNF), an autologous protein having a molecular weight of about 17,000, is a product synthesized by macrophages, secreted by these cells in response to the presence of endotoxin. TNF serves two entirely separate functions in tumor-bearing mammals.

On the one hand, TNF has a direct cytotoxic effect on the tumor cells (tumor-toxicity), while, on the other hand, TNF causes the body's reserve forces to be released, which in chronic cases leads to serious emaciation (cachexia) of the patient and other symptoms of endotoxic shock. The two responses to TNF doses, the tumor-toxic effect, on the one hand, and the cachectic effect, on the other hand, are by no means represented to the same extent in all species. Thus, while the mouse appears to be relatively resistant to cachexia and sensitive to the tumor-toxic properties of TNF, in man the situation is the reverse. Thus, systemic administration of TNF leads more to cachexia and endotoxic shock than to a remission in tumor patients.

On regional perfusion of the liver there can be locally achieved an about 35-fold increase of the normal systemic dose, since the liver only amounts to about 3% of the total body mass. However, by using the device of to the invention, more specifically in the form of the so-called Aigner catheter in the Vena cava, and passing the blood over a suitable filter having a sufficient capacity, the excessive active substance is removed to a great extent. Thus it is also possible, accordingly to increase the dose of the active substance to be applied. TNF is introduced through the artery into the liver by means of a permanent catheter. In a corresponding efferent vessel, the Vena cava, there is inserted an Aigner catheter. By means of this double catheter the blood is withdrawn and forced through an anti-TNF filter consisting of matrix-bound anti-TNF-monoclonal antibodies.

What is claimed is:

1. A device for removing a substance from the human circulatory system comprising (a) a first catheter having one end positionable in a blood vessel distally from a tumor for removing blood from the vessel, (b) a second catheter having one end positionable in the blood vessel for returning blood to the vessel and forming with the first catheter a double catheter along at least part of their length such that the one end of the first catheter is joined to the second catheter at a distance from the one end of the second catheter, (c) a pump connected to the first and second catheters, (d) at least one container holding immobilized antibodies to the substance and connected to the first and second catheters such that blood passes from the first catheter to the second catheter through the container, and (e) an inflatable balloon for blocking the blood vessel when inflated and located on the second catheter between the end of the first catheter and the end of the second catheter.

2. A device according to claim 1 further comprising a second balloon located on the double catheter for blocking the blood vessel.

3. Device according to claim 1, characterized in that the immobilized antibody present in the container is directed against active substances of blood cells and/or blood cell precursors.

4. Device according to claim 1, characterized in that the immobilized antibody present in the container is active against lymphokines, monokines and/or cytokines.

5. Device according to claims 1, characterized in that the immobilized antibody present in the container is directed against interferons, interleukins, colony stimulating factors, tumour necrosis factor, lymphotoxin and/or transforming growth factors.

* * * * *